United States Patent [19]

Juhn

[11] 4,334,538

[45] Jun. 15, 1982

[54] ASPIRATOR FOR COLLECTING LIQUID SAMPLES

[76] Inventor: Steven K. Juhn, 2624 Rice Creek Ter., New Brighton, Minn. 55112

[21] Appl. No.: 103,072

[22] Filed: Dec. 12, 1979

[51] Int. Cl.³ .............................................. A61M 1/00
[52] U.S. Cl. ..................................... 128/276; 433/95; 128/760
[58] Field of Search ............... 128/276, 277, 760, 763, 128/765, 766, 77, 215; 433/92, 95; 528/288

[56] References Cited

U.S. PATENT DOCUMENTS

| | | | |
|---|---|---|---|
| 2,219,089 | 10/1940 | Everett | 128/215 |
| 2,953,243 | 9/1960 | Roehr | 128/215 |
| 3,050,062 | 8/1962 | Ulmer | 128/276 |
| 3,766,907 | 10/1973 | Muenzer | 128/760 |
| 3,889,682 | 6/1975 | Denis et al. | 128/276 |
| 3,911,919 | 10/1975 | Raitto | 128/276 |

FOREIGN PATENT DOCUMENTS

| | | | |
|---|---|---|---|
| 2805285 | 8/1978 | Fed. Rep. of Germany | 128/276 |
| 1019560 | 2/1966 | United Kingdom | 128/276 |

OTHER PUBLICATIONS

"Nylons–Polyamides", Modern Plastics Encyclopedia, McGraw-Hill, N.Y., N.Y., Resins and Molding Compounds, 1967, pp. 169–172.

Primary Examiner—Robert W. Michell
Assistant Examiner—J. L. Kruter
Attorney, Agent, or Firm—Arthur G. Yeager

[57] ABSTRACT

An aspirator for manually collecting liquid samples, particularly for medical purposes, comprising a handle connected to a vacuum source and having a sample collection vial fitting into a cavity in the handle with a finger control vent in the cavity and having a tubing to function as the probe for the sample to be collected, the tubing leading into the sample collection vial.

7 Claims, 9 Drawing Figures

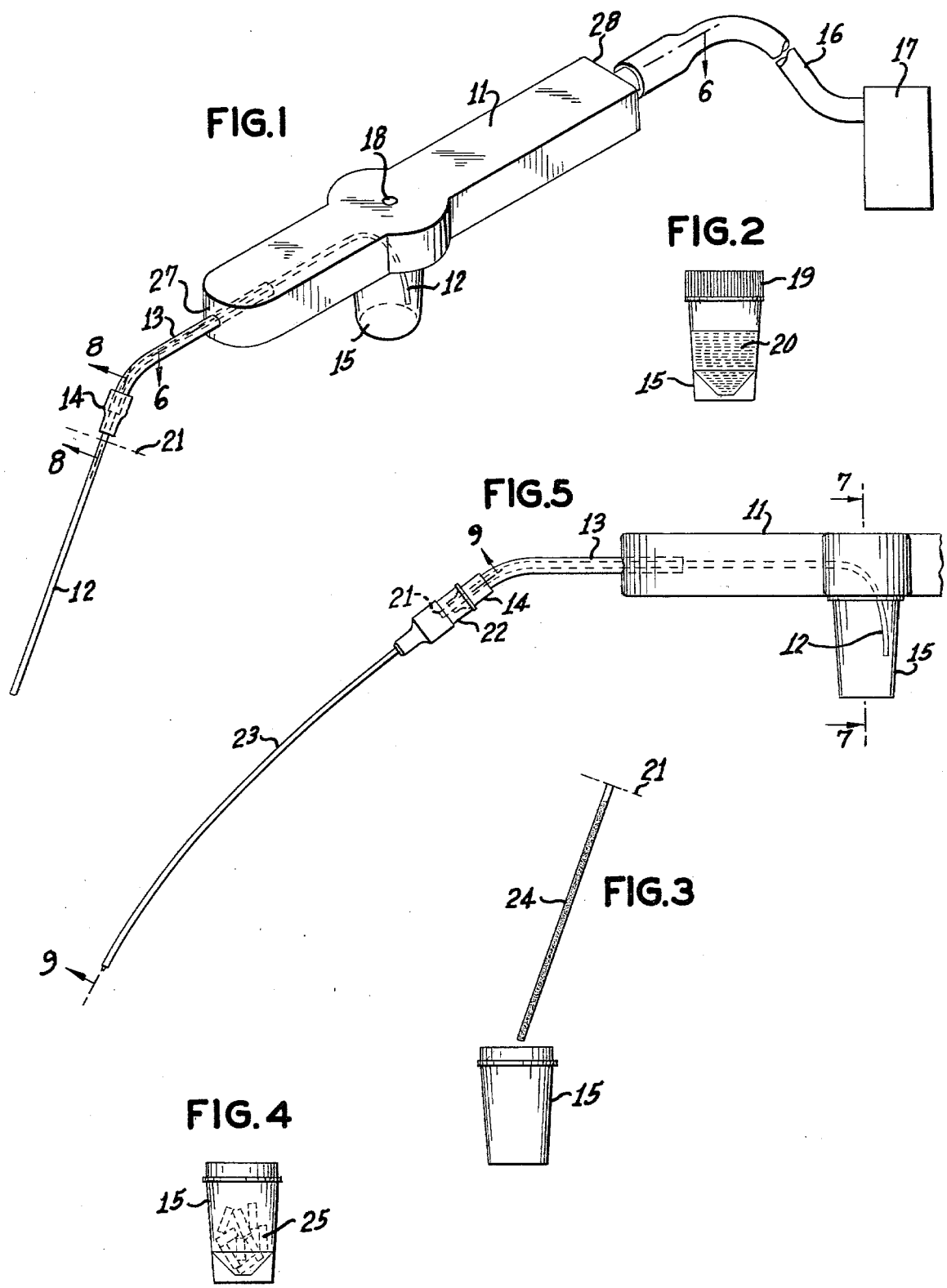

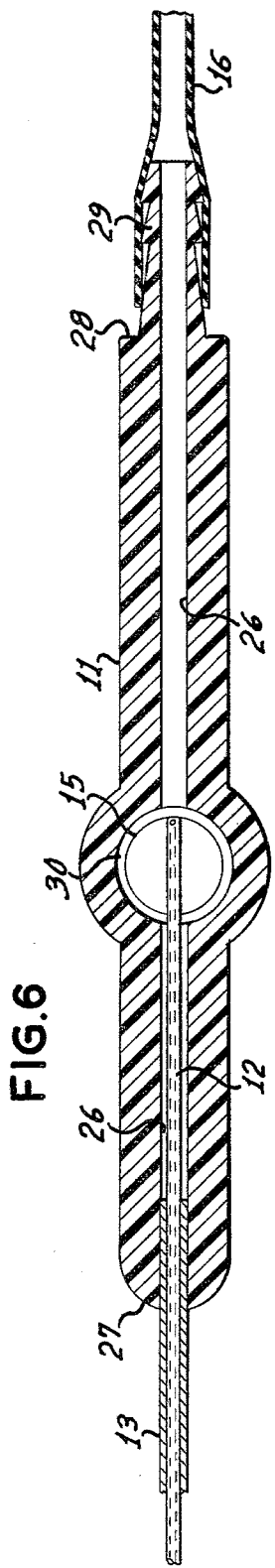
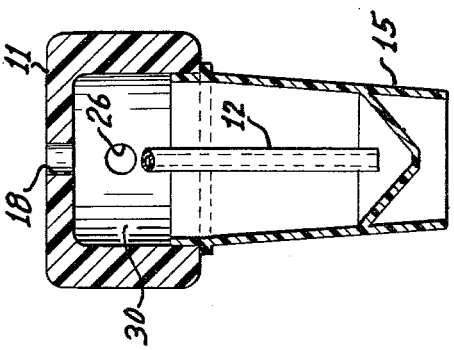
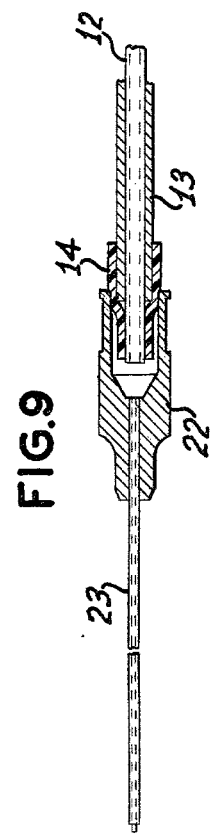

ASPIRATOR FOR COLLECTING LIQUID SAMPLES

BACKGROUND OF THE INVENTION

There are occasions when it is desirable or necessary to obtain a small specimen of a liquid from a location which is difficult to reach. Important examples of such instances are found in the diagnosis of various diseases, infections and other ailments of the human body. While instruments of various types have been employed in the past to collect samples for medical analysis they have, in general, been of a permanent type requiring sterilization after each use. The modern tendency is to employ instruments which may be used once and discarded so as to avoid the high cost of assembly, sterilization, and repackaging to maintain the sterile condition.

It is an object of the present invention to provide a nonreusable aspirator designed to collect small specimens of liquid samples, particularly from the human body. It is a particular object of this invention to provide such an instrument for use in collecting liquid samples from the middle ear. Otitis media is a middle ear infection which is extremely common and manifests itself with the presence of fluid in the middle ear. This fluid may be serous, purulent, or mucoid and may arise as a result of several different circumstances or etiologies. In order to properly treat the patient it is important to collect a sample of the fluid and analyze it. The present invention involves a simple, inexpensive apparatus which can be employed to collect such a fluid into a sample vial which can then be sent for suitable analysis and the entire apparatus thrown away.

BRIEF SUMMARY OF THE INVENTION

This invention, contemplates an aspirator for manually collecting samples of fluids from remote cavities comprising an elongated handle having a top, a bottom, a forward end, a rearward end, a centrally located cavity opening on the bottom of the handle, a passageway communicating said cavity with both said forward and said rearward ends, and a aspiration controlled finger vent communicating said cavity with said top; a removable specimen collecting vial having an open top attaching to said cavity with an airtight fitting; a removable flexible tube means extending from said cavity through said passageway and out and beyond said forward end for a selected distance, said tube means providing an airtight seal with said passageway; and said rearward end being adapted for connection of said passageway to a source of vacuum. In specific embodiments of this invention the aspirator is designed for collection of liquids from the middle ear of a human by employing either a flexible plastic tube or a Luer-Lok hypodermic needle to reach into the middle ear cavity through the tympanic membrane.

BRIEF DESCRIPTION OF THE DRAWINGS

The novel features believed to be characteristic of this invention are set forth with particularity in the appended claims. The invention, itself, however, both as to its organization and method of operation, together with further objects and advantages thereof, may best be understood by reference to the following description taken in connection with the accompanying drawings in which:

FIG. 1 is a perspective view of the apparatus of this invention.

FIG. 2 is an elevation view of the specimen collection vial containing a liquid sample and being closed by a cap for handling purposes.

FIG. 3 is a elevation view of the specimen vial of this invention ready to receive viscous fluid which must be expelled from the tube into the vial.

FIG. 4 indicates an alternative means for collecting a specimen shown in FIG. 3 wherein the tubing containing the viscous liquid is cut into small pieces.

FIG. 5 is a partial elevation view showing the device of this invention with a Leur-Lok hypodermic needle attached thereto.

FIG. 6 is a cross sectional view taken along line 6—6 of FIG. 1.

FIG. 7 is a cross sectional view taken along line 7—7 of FIG. 5.

FIG. 8 is a cross sectional view taken along line 8—8 of FIG. 1.

FIG. 9 is a cross sectional view taken along line 9—9 of FIG. 5.

DETAILED DESCRIPTION OF THE INVENTION

The general features of this invention can best be understood with respect to FIG. 1. The apparatus comprises a generally elongated handle 11 which has an internal passageway leading from its forward end 27 and from its rearward end 28 to a central cavity which is on the bottom of handle 11 and which fits collection vial 15. The passageway at the rearward end 28 of handle 11 is connected to a source of vacuum 17 by a flexible tube 16. The passageway at the forward end 27 of handle 11 is connected to a flexible tube 12 which extends from sample vial 15 to some selected distance beyond forward end 27 which is necessary and desirable to reach the cavity from which the liquid specimen is to be collected. In the embodiment shown in this drawing there is employed a soft metal tube 13 which fits into the passageway in handle 11, and through the center of tube 13 is threaded a soft flexible plastic tube 12. The relative dimensions of metal tube 13 and plastic tube 12 are such that they provide an airtight seal with respect to the passageway in handle 11 at forward end 27. There is also shown in this drawing cuff 14 which is a short length of soft tubing fitting over the free end of metal tube 13 and the forward extension of plastic tube 12. Cuff 14 serves the purpose of providing a seat for a metallic hypodermic needle as shown in FIG. 5 and will be discussed below.

On the upper surface of handle 11 there is an aspiration control finger vent 18 which communicates with the cavity in the bottom of handle 11 into which sample vial 15 fits. This vent permits the operator of the device to apply suction through tube 12 when his fingers closes vent 18 to the atmosphere. When vent 18 is left uncovered, however, the vacuum is essentially broken with respect to 12 because vacuum from source 17 pulls air from the atmosphere through vent 18 rather than through the more tortuous path of tubing 12.

In FIG. 2 there is shown a specimen collection vial 15 containing a liquid specimen 20 and closed with a cap 19 to make the vial suitable for handling without contamination or loss of its contents. As will be seen in other drawings such as FIGS. 3, 4, and 7, vial 15 is made with a neck at its open end and a projecting collar which permits vial 15 to be inserted into a corresponding cavity in the bottom of handle 11 to produce a connection which is substantially airtight.

In some instances the fluid which is collected as a specimen may be of a thick viscous nature which will not readily flow through the internal diameter of tubing 12. If the liquid is sufficiently fluid to fill a portion of tubing 12, such as for example shown in FIG. 3 at 24 the liquid may be expelled from the tube in vial 15 by applying pressure to the tube or by squeezing between tweezers or pliers to force the fluid out of the tubing. If the collective liquid is even more viscous so that it approaches a semisolid condition it is entirely feasible to merely cut the filled tubing into short lengths as shown in FIG. 4 and submit the specimen in that form for analysis.

In some instances, the surgeon may wish to employ a hypodermic needle to puncture the tympanic membrane and to remove the sample. For such purposes the Leur-Lok needle can be employed as shown at 23 in FIG. 5. This type of needle has a socket 22 and it is for purposes of seating this socket that cuff 14 is employed. In this instance tubing 12 is severed as shown at 21 near the end of cuff 14. Needle 23 can then be manually seated over cuff 14 to produce a rigid airtight seal. Cuff 14 is preferably made of a silicone rubber which is soft and pliable and serves well in this embodiment.

In FIG. 6 the details of construction of the device of this invention can be readily understood. Handle 11 contains a central cavity 30 and a passageway 26 which extends from the forward end 27 to cavity 30 and from the rearward end 28 to cavity 30. At rearward end 28 there is shown a typical fitting 29 designed for the attachment of flexible tubing 16 to produce an airtight fitting so that vacuum may be drawn through the hollow portion of tubing 16 and passageway 26. Inserted into passageway 26 in forward end 27 is a soft metal tube 13 which typically may be aluminum. Through the hole in tubing 13 is inserted a soft flexible tubing 12 extending from vial 15 in cavity 30 through tubing 13 and beyond to whatever selected distance is preferred. The dimensions of flexible tube 12, metal tube 13 and passageway 26 are such that a substantially airtight fitting is obtained by manually assembling tubes 12 and 13 into passageway 26. Tube 12 is preferably made of polyamide. Handle 11 is preferably made of an injection moldable grade of polyamide. Flexible tubing 16 may be made of rubber, polyamide, or the like.

In FIG. 7 there is shown another view of the cross section through handle 11 and vial 15 of this device. Handle 11 contains cavity 30 into which enters passageway 26 and finger vent 18. It may be seen that tube 12 terminates near the bottom of vial 15 and that any vacuum applied through passageway 26 will be transmitted through tube 12 if finger vent 18 is closed.

In FIGS. 8 and 9 there are seen the details of the attachment between flexible tube 12 and soft metal tube 13 as well as the positioning of cuff 14. So long as flexible tube 12 is employed to collect the specimen; cuff 14 is not a necessary component since the dimensions of flexible tube 12 and metal tube 13 are such that airtight connection can be made when metal tube 13 is inserted into forward end 27 of handle 11. When a hypodermic needle is to be employed rather than the free end of flexible tube 12 to collect the specimens, cuff 14 is necessary. The end of tube 12 is severed close to the end of cuff 14 and this provides a suitable seat for socket 22 of a Luer-Lok hypodermic needle 23.

This device is eminently suitable for use with a myringotomy incision when tube 12 is employed to collect fluid from the middle ear. If the surgeon prefers to employ a hypodermic needle, e.g. for purposes of tympanocentesis, the needle may be employed to puncture the tympanic membrane and the sample collected. It is of course entirely possible that the device of this invention can be employed for collecting fluid samples from other locations whether they be from human cavities that are difficult to reach or from cavities which are difficult to reach and wherein a small sample, e.g. 1-2 cc, is to be collected. Such might be the case in a variety of laboratory techniques, for dental purposes, for veterinarian purposes, etc.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what is desired to secure by Letters Patent of the United States is:

1. An aspirator for manually collecting samples of fluids from remote human body cavities comprising an elongated axially extending handle having a top surface, a bottom surface, a forward end, a rearward end, a centrally located cavity opening through said bottom surface of said handle, said handle between said cavity and said rearward end providing means for manually gripping thereof, a rigid passageway extending through said handle communicating said cavity with said forward end and said rearward end, said handle having an aspiration control finger vent located directly above the cavity and communicating with said cavity and said passageway through said top surface; a removably attached specimen collecting vial having an open top in air-tight attachment to said cavity; a separate removable flexible tube means extending from within said cavity and vial through said passageway and outwardly beyond said forward end for a predetermined distance, said tube means including means for providing an airtight seal with said passageway; a removable length of a metal hollow tube extending outwardly from said forward end and encircling said flexible tube in an air-tight manner; and said rearward end including means for connecting said passageway to a source of vacuum.

2. The aspirator of claim 1 which additionally contains a soft resilient tubular cuff fitting over the free end of said metal tube and a metallic hollow collection needle having a coupling socket, said cuff serving as a deformable air tight seat for the attachment of said socket thereto.

3. The aspirator of claim 2 wherein said needle is a Luer-Lok hypodermic needle.

4. In a fluid aspirator-collector, the combination of an elongated barrel means forming a handle for gripping thereof and having a first end, a second end, a top surface, a bottom surface, a cavity opening outwardly through said bottom surface intermediate said ends, a longitudinal passageway extending from each of said ends and intersecting said cavity, and an aspiration control thumb vent from said top surface extending into said cavity; a removable metal hollow pipe extending from said first end and having its central passage in communication with said passageway and having a free end disposed outwardly beyond said first end and an opposite end located within said passageway; a specimen collection vial removably attached to said handle in air-tight communication with said cavity; and a flexible tube inserted through said central passage of said pipe and being air-tight with respect thereto, said tube extending from said cavity and vial to a free end a predetermined distance beyond said free end of said pipe said second end including means for connecting said passageway to a source of vacuum.

5. The combination according to claim 4 wherein said collection tube is of readily severable plastic.

6. The combination according to claim 4 wherein a soft, resilient, tubular cuff encircles said free end of said pipe.

7. The combination according to claim 6 wherein said free end of said collection tube is adjacent said cuff whereby the exterior proportions of said tube and said cuff are adapted to receive the socket of a standard Luer-Lok hypodermic needle.

* * * * *